United States Patent [19]

Lewis

[11] Patent Number: 4,950,263
[45] Date of Patent: Aug. 21, 1990

[54] UNIVERSAL HINGED CONTROL DIAPER

[76] Inventor: Debra K. Lewis, 6839 SW. 114th Pl., Unit B, Miami, Fla. 33173

[21] Appl. No.: 290,632

[22] Filed: Dec. 27, 1988

[51] Int. Cl.⁵ ............................................. A61F 13/16
[52] U.S. Cl. ................................................ 604/385.1
[58] Field of Search ............... 604/385.1, 387, 395, 604/399, 398, 393

[56] References Cited

U.S. PATENT DOCUMENTS

| | | | |
|---|---|---|---|
| 2,595,507 | 5/1952 | Beck | 604/395 |
| 2,977,957 | 4/1961 | Clyne | 604/398 |
| 3,559,648 | 2/1971 | Mason, Jr. | 128/287 |
| 3,672,371 | 6/1972 | Roeder | 604/387 |
| 4,022,212 | 5/1977 | Lovison | 604/395 |
| 4,265,245 | 5/1981 | Glassman | 128/287 |
| 4,338,939 | 7/1982 | Daville | 604/399 |
| 4,501,587 | 2/1985 | Enloe | 604/385 |
| 4,585,448 | 4/1986 | Enloe | 604/378 |
| 4,609,373 | 9/1986 | Johnson | 604/387 |
| 4,615,695 | 10/1986 | Cooper | 604/385 |
| 4,643,726 | 2/1987 | Gegelys | 604/368 |
| 4,820,296 | 4/1989 | Masliyah | 604/385.1 |
| 4,838,886 | 6/1989 | Kent | 604/393 |

*Primary Examiner*—David J. Isabella
*Attorney, Agent, or Firm*—Oltman and Flynn

[57] ABSTRACT

The diaper is constructed of an elongate, substantially rectangular, main moisture-absorbent layer shaped as a "U", having a front, bottom and rear section; an outer liner of an impermeable material attached to the outer surface of the main layer; a flap of a highly moisture-absorbent material hingedly attached to a central area on the inner surface of the bottom section, and straps attached to the front or rear section for holding the diaper together when it is in place on a user.

4 Claims, 1 Drawing Sheet

UNIVERSAL HINGED CONTROL DIAPER

The invention relates to a diaper, and more particularly to a diaper having a moveable flap that can be shifted to one or the other side to accommodate a male or a female user.

BACKGROUND AND PRIOR ART

In the evolution of diapers for children and adults, the diaper has changed from the early single sheet of woven cotton or linen to a more complex construction composed of several layers, including an outer thin liner of impermeable material, and an inner thick layer of a highly moisture-absorbent material, such as cotton or cellulose.

In the interest of providing a more comfortable diaper of the later construction, it has become known to form the absorbent layer as a thinner absorbent layer for the entire area of the diaper, and to compensate for loss of total absorbent material place a thicker highly absorbent padded area in the crotch area of the diaper. A diaper of such construction is shown in U.S. Pat. No. 4,501,587 and in U.S. Pat. No. 4,585,448.

The diapers according to the known art as exemplified in aforesaid U.S. Patents have the drawbacks that the diapers must be fabricated in two different types, namely one for boys and one for girls, or one for men and one for women, since in the male type the extra protection must be in front and the female type the extra protection must be in the center. Also, it must be stocked by manufacturers, vendors and often users such as nursing homes and hospitals in two different types.

The need to stock two different types leads to higher cost and need for more inventory and inconvenience in added handling.

It is the object of the instant invention to provide a single universal type diaper that is equally useable for both male and female users and thereby eliminate the above described disadvantage of having two types of diapers.

SUMMARY OF THE INVENTION

The diaper according to the instant invention is constructed of an elongate, substantially rectangular, main moisture-absorbent layer shaped as a "U", having a front, bottom and rear section; an outer liner of an impermeable material attached to the outer surface of the main layer; a flap of a highly moisture-absorbent material hingedly attached to a central area on the inner surface of the bottom section, and straps attached to the front or rear section for holding the diaper together when it is in place on a user.

In accordance with a further feature, the diaper has an inner liner permeable to moisture for admitting urine to the absorbent main layer.

In accordance with another feature, the flap is also covered with a permeable liner.

In accordance with still another feature, the central area of attachment for the flap is a rectangular area, reaching from one side of the diaper to the other.

In accordance with a still further feature, the central area is offset to the front section approximately 0.5–1.5 inches.

Other objects of this invention will appear from the following description and appended claims, reference being had to the accompanying drawings forming a part of this specification wherein like reference characters designate corresponding parts in the several views.

DESCRIPTION OF THE PREFERRED EMBODIMENT

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

Figure 2:
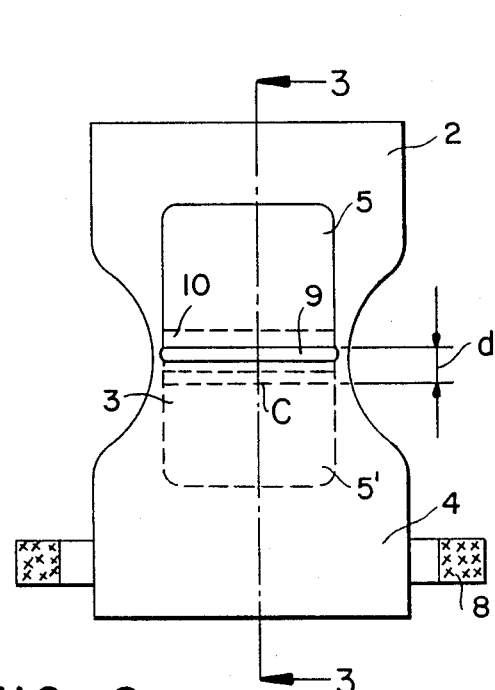
FIG. 2 is a plan view of the invention showing its general outline.
Figure 3:
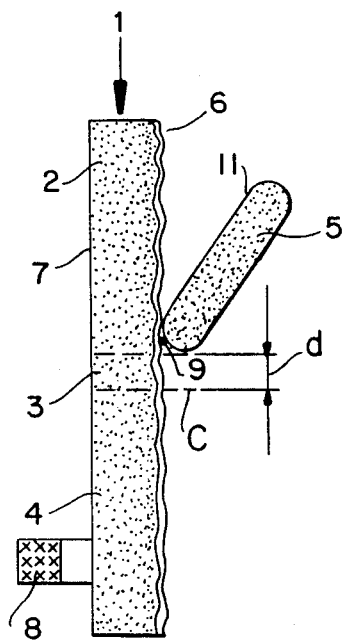
FIG. 3 is an edge view of the invention seen along the line 3—3 of FIG. 2 showing it unrolled.
Figure 4:
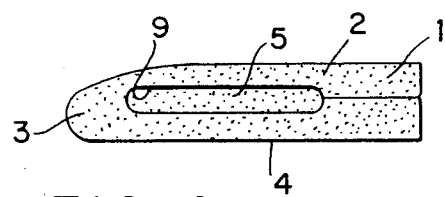
FIG. 4 is a diagrammatic cross-sectional view of the invention showing it folded together for storage or shipping.

In the Figures, the diaper according to the invention is seen in a side view formed in a "U" shape as it will appear when it is on a person. It has a moisture-absorbent thick main layer 1, having an inner surface and an outer surface. The outer surface has attached thereto an impermeable liner 7 which contains moisture absorbed in the main layer 1, and it may optionally have an inner permeable liner 6 which admits urine to the absorbent layer 1. The main layer 1 has a front section 2 to be arranged against the anterior side of the body of the wearer, a bottom section 3 arranged in the crotch area and a rear section 4 arranged against the posterior side of the body. The absorbent layer 1 is made of a highly absorbent material such as cotton, cellulose or other suitable hygroscopic fibrous, readily compressible material. The absorbent layer 1 is advantageously cut as a generally hourglass-shaped sheet, as shown in FIG. 2 in order to reduce the amount of material in the crotch area. The impermeable liner 7 is advantageously of a thin plastic water tight material. The permeable inner liner 6, if provided, is advantageously made of a thin woven or foamed material.

Figure 1:
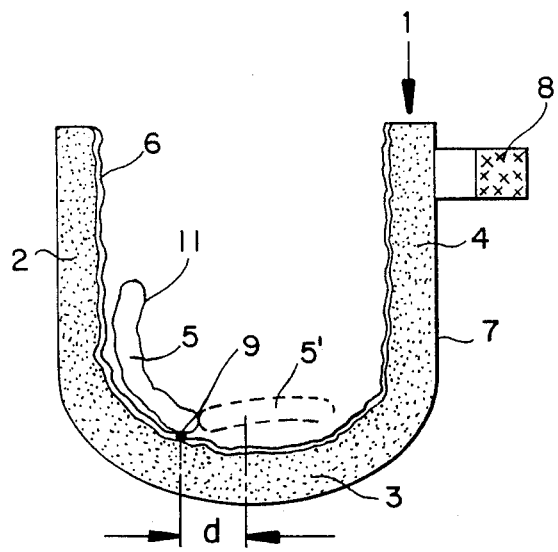
FIG. 1 is a diagrammatic cross-sectional view of the invention seen along the line 3—3 of FIG. 2 showing the interior construction.

A flap 5 is attached by a hinge-like strip 9 disposed transversely between the lateral sides of the diaper, so that the flap 5 can readily be placed in a forward position as shown in FIGS. 1 and 2 or in a center position 5', shown in phantom lines. The strip 9, made of a thin, flexible material assures that the flap stays in place during use. The strip 9 is advantageously attached to the absorbent layer 1 or to the inner liner 6 is a central area 10 of the bottom section 3 by stitching or by adhesive means. The flap 5 is made of a highly absorbent material, advantageously of material of a cohesive consistency and it may be lined by a permeable liner 11, which may be completely enclosing the flap 5. The central area 10 is advantageously offset a distance d in direction of the forward section 2, wherein d is typically within the range of 0.5 to 1.5 inches, which provides a better more central placement of the flap 5 in relation to the exposed parts of the diaper, both when it is used for males and females. The diaper according to the invention is readily folded or rolled into a compact flat package for storage and packing as shown in FIG. 5.

The outer and inner liners 6, 7 may advantageously be attached to the main layer 1 by stitching or adhesive means. Two straps 8 are provided, sewn or adhered to one end of the diaper, and serve to be attached to the outer liner near the other end of the diaper, by adhesion, Velcro ® or other suitable means, for holding the diaper together when in place on a person.

I claim:

1. An absorbent diaper comprising:
    an U-shaped main body having front, bottom and rear sections, said main body being a composite formed of an absorbent layer having inner and outer surfaces and an outer impermeable liner attached to said outer surface; and
    a separate absorbent pad having an edge hingedly attached to a central area of the inner surface of said bottom section such that the pad acts as a flap which may be selectively placed in a forward frontal position or a central bottom position to accommodate either a male or female user, respectively, said central area being offset a predetermined distance in a direction toward said front section; and
    fastening means for connecting together the front and rear sections about the torso of the user.

2. An absorbent diaper according to claim 1 wherein said predetermined distance is within the range of 0.5 to 1.5 inches.

3. An absorbent diaper according to claim 1 wherein the diaper is disposable.

4. An absorbent diaper according to claim 1 wherein said bottom section is narrower than the front and rear sections.

* * * * *